United States Patent [19]
Reichenberger et al.

[11] Patent Number: 4,976,255
[45] Date of Patent: Dec. 11, 1990

[54] APPARATUS FOR EXTRACORPOREAL LITHOTRIPSY USING SHOCK WAVES AND THERAPEUTIC ULTRASOUND

[75] Inventors: Helmut Reichenberger, Eckental; Georg Naser, Zinrdorf; Erhard Schmidt, Erlangen, all of Fed. Rep. of Germany

[73] Assignee: Siemens Aktiengesellschaft, Berlin and Munich, Fed. Rep. of Germany

[21] Appl. No.: 393,789

[22] Filed: Aug. 15, 1989

[30] Foreign Application Priority Data

Aug. 17, 1988 [EP] European Pat. Off. ........... 88113376

[51] Int. Cl.$^5$ .............................................. A61B 17/22
[52] U.S. Cl. ................................................. 128/24 A
[58] Field of Search ........... 128/24 A, 24 EL, 660.03; 606/127, 128

[56] References Cited

U.S. PATENT DOCUMENTS

| | | | |
|---|---|---|---|
| 4,658,828 | 4/1987 | Dory | 128/660.03 |
| 4,745,920 | 5/1988 | Forssmann et al. | 128/24 A |
| 4,771,787 | 9/1988 | Wurster et al. | 128/660.03 |
| 4,844,079 | 7/1989 | Naser et al. | 128/660.03 |

FOREIGN PATENT DOCUMENTS

| | | | |
|---|---|---|---|
| 280088 | 2/1988 | European Pat. Off. | 128/24 A |
| 3328068 | 2/1985 | Fed. Rep. of Germany | 128/24 A |

*Primary Examiner*—Kyle L. Howell
*Assistant Examiner*—Kevin Pontius
*Attorney, Agent, or Firm*—Hill, Van Santen, Steadman & Simpson

[57] ABSTRACT

An apparatus for extracorporeal lithotripsy has one or more shock wave sources for generating shock waves converging at a focus zone in which a calculus to be disintegrated is located in a patient, and additionally has a therapeutic ultrasound source for generating ultrasound waves focused at a focus zone substantially coinciding with the focus zone of the shock wave source. The ultrasound waves generated by the therapeutic ultrasound source have a sufficiently high energy to be effective for assiting in disintegrating the calculus, as contrasted with ultrasound waves used to obtain an ultrasound image. The shock wave source and the therapeutic ultrasound source can be driven from a generator stage connected both sources, which is capable of driving the sources simultaneously or in selected chronological succession, such as in alternation.

23 Claims, 7 Drawing Sheets

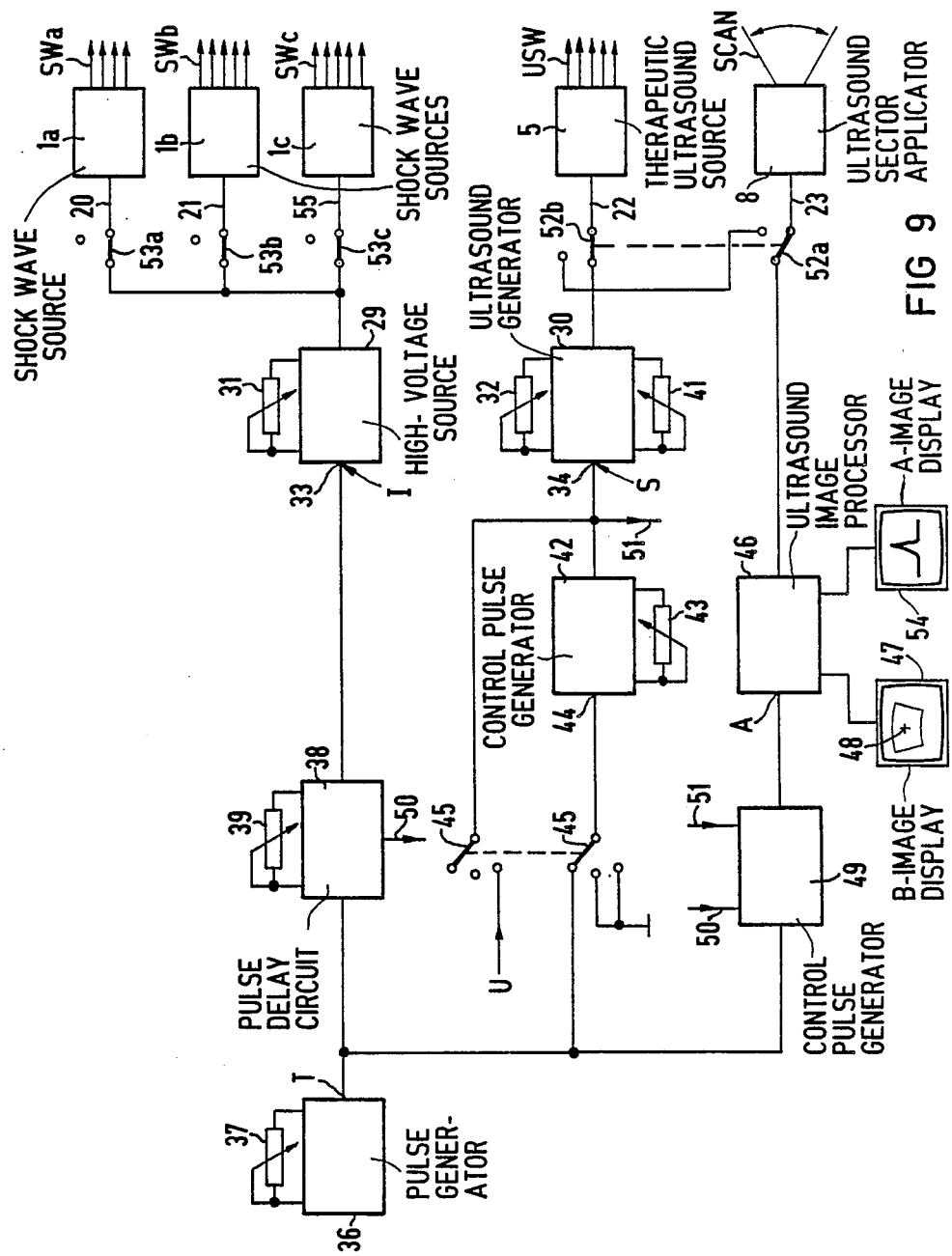

APPARATUS FOR EXTRACORPOREAL LITHOTRIPSY USING SHOCK WAVES AND THERAPEUTIC ULTRASOUND

BACKGROUND OF THE INVENTION

1. Field of the Invention

The present invention is directed to extracorporeal lithotripsy devices, and in particular to such devices making use of a shock wave source applied against the body of a patient.

2. Description of the Prior Art

It is known to use a source of shock waves, applied against the body of a patient, to cause focused shock waves to converge within a zone at wich a calculus, such as a kidney stone or a gall stone, is located. The calculus disintegrates into fragments by the action of the shock waves, and the fragments can be eliminated (excreted) naturally, or can be completely or partially dissolved using chemotherapeutic measures (litholysis).

An apparatus of this type is described in U.S. Pat. No. 4,674,505 which includes a shock wave source which generates shock waves converging in a focus zone lying on the acoustic axis of the shock wave source. The apparatus also includes a generator and a control circuit for driving the shock wave source. The shock wave source includes means for acoustically coupling the source to the body of the patient into whom the shock wave are to be introduced, and for adjusting the apparatus and body of the patient relative to each other.

This apparatus achieves good results in the treatment of kidney stones without having recourse to additional chemotherapeutic measures. It is nonetheless desired to increase the effectiveness of this known apparatus. In this context, an increased effectiveness means a reduction in the required number of shock waves to treat a calculus with a simultaneously increase in the degree of disintegration. Such an increased effectiveness results in a shortened treatment time and simultaneously assures that the calculus (or calculi) will be disintegrated into smaller fragment which can be more easily eliminated or, if necessary, can be more quickly dissolved with chemotherapeutic measures, because the surface area to volume ratio becomes larger as the fragments become smaller. Such an increased effectiveness thus means that the stress on the patient from the treatment is lower because not only is the dose of acoustic energy diminished (a treatment with shock waves can produce a sensation of pain, potential skin redness and, under certain circumstances, hetatoma) but also the medication stress on the patient due to chemotherapeutic measures is reduced, or even eliminated (such chemotherapeutic measures sometime being required over a number of months). It is known to therapeutically treat certain kidney stone afflictions using focused shock waves, and efforts have also been made to treat gall stones by extracorporeal lithotripsy, as described in the article "Framentation of Gallstones By Extracorporeal Shock Waves," Sauerbruch et al., The New England Journal of Medicine, Mar. 27, 1986, pages 818-822. The nature and composition of gall stones, however, is different from that of kidney stones, and the effectiveness of known extracorporeal lithotripsy devices is not sufficient to destroy gall stones, using a number of shock waves which is acceptable to the patient's comfort, which results in disintegration of the gall stones to such an extent that the fragments can be naturally eliminated. Chemotherapeutic measures for partially or completely dissolving the fragments are therefore required. It is therefore a problem in the art to improve the effectiveness of extracorporeal lithotripsy devices to permit fragmentation of gall stones to an extent so that chemotherapeutic measures can be eliminated, or at least substantially reduced.

Experiments have also been undertaken in an effort to disintegrate urinary and biliary calculi using ultrasound energy as reported in "The Application of Ultrasound Energy to Urinary and Biliary Calculi," Coats, The Journal of Urology, Vol. 75, No. 5, May 1956, pages 865-874. Experiments were conducted in an effort to disintegrate gall stones in a laboratory simulation, the stones having been surgically removed from patients. The reported results stated that some additional (i.e., additional to the ultrasonic energy alone) physical force was required to disintegrate the calculi. Experiments were also reported in this article which were undertaken in an effort to disintegrate gall stones in living tissue. These experiments were unsuccessful, and the author concluded that ultrasonic treatment of calculi by the application of the energy source at the surface of the body seems impractical because, even with a focused crystal, the power required to penetrate from the surface to the calculus-containing organs, and to impress an adequate power dosage on the stone, would certainly be lethal to the intervening tissues and organs.

The application of ultrasound energy to accelerate human gall stone dissolution was reported in an abstract by Griffith et al. in The Journal of the Acoustical Society of America, Supplement 1, Vol 81, Spring 1987. It was reported that using a cholesterol stone solvent as the primary dissolving agent, dissolution of gall stones could be accelerated by the additional application of ultrasound energy.

SUMMARY OF THE INVENTION

It is an object of the present invention to provide an extracorporeal lithotripsy apparatus which achieves improved effectiveness in comparison to conventional devices i.e., achieves an increased degree of calculus fragmentation with a reduced number of shock waves, so that the stress on the patient due to the treatment is diminished and that chemotherapeutic measures are superfluors, or are required only to a reduced degree.

The above object is achieved in accordance with the principles of the present invention in a lithotripsy apparatus having at least one shock wave source for generating focused shock waves converging in a first focus zone lying on the acoustic axis of the shock wave source, and a therapeutic ultrasound source for generating ultrasound waves converging in a second focus zone lying on the acoustic axis of the therapeutic ultrasound source. The shock wave source and the ultrasound source are arranged so that their respective focus zones substantially coincide and the overall apparatus is positioned relative to a patient so that a calculus to be disintegrated is located within the coinciding focus zones. The apparatus includes a generator stage for driving both the shock wave source (or shock wave sources) and the therapeutic ultrasound source, and means for acoustically applying the apparatus to the body of a patient so that both the shock waves and the ultrasound waves can be coupled into the patient's body.

The generator stage includes control circuitry which permits the therapeutic ultrasound source and the shock wave source to be driven simultaneously, or in a selected chronological succession, such as in alternation.

The apparatus disclosed and claimed herein causes the calculus to be disintegrated both by the action of the focused shock waves and the action of the focused ultrasound waves. The focused ultrasound waves subject the calculus to mechanical stresses which are different from the mechanical stresses caused by the action of the shock waves on the calculus. The resultant mechanical stresses which occur given combined application of shock waves and ultrasound waves achieves an increased effectiveness in the apparatus, i.e., the number of shock waves for a successfully treatment is reduced with a simultaneous increase in the degree of fragmentation. The stress on the patient caused by the acoustic energy, particularly the shock waves, is thus considerably reduced. As a consequence of the greater degree of fragmentation, gall stones, in particular, can be disintegrated to such an extent that natural elimination of the fragments is possible, or at least the use of additional chemotherapeutic measures, and the resultant stresses on the patient, can be considerably reduced. Because shock waves and ultrasound waves can be generated simultaneously or alternatingly in chronological succession in the apparatus disclosed and claimed herein it is possible to adapt the treatment to the nature of the calculus to be disintegrated. It is possible, for example, to drive the therapeutic ultrasound source so that it generates ultrasound waves as continuous sound, on which a sequence of shock waves generated with the shock wave source is superimposed. An especially high degree of fragmentation is achieved by driving the therapeutic ultrasound source so that is generates ultrasound waves as intermittent continuous sound, i.e., in a form referred to as ultrasound bursts, and the shock wave source is operated to generate a shock wave during each ultrasound burst, particularly in the second half of the chronological duration of the ultrasound burst. Another effective manner of operation is to generate a shock wave directly following each ultrasound burst.

In a preferred embodiment of the apparatus, the shock wave source, the therapeutic ultrasound source and, if desired, an ultrasound imaging applicator which is part of an ultrasound locating apparatus, are arranged in a common carrier, so that a compact device which is easy to manipulate is achieved, which consequently can be accurately applied to the body of a patient.

As used herein, the term "therapeutic ultrasound source" is intended to be different from a conventional ultrasound source of the type used to conduct an ultrasound scan to generate an ultrasound image. In comparison to such a scanning ultrasound source, the "therapeutic ultrasound source" used in the apparatus disclosed herein is an ultrasound source which generates ultrasound waves at a significantly higher intensity (for example, higher by a factor of ten) than ultrasound sources which are used for diagnostic purposes, such as for imaging.

DESCRIPTION OF THE DRAWINGS

FIG. 9 is a block circuit diagram of a generator stage for operating the extracorporeal lithotripsy apparatus shown in FIGS. 6–8.

DESCRIPTION OF THE PREFERRED EMBODIMENTS

Figure 1:
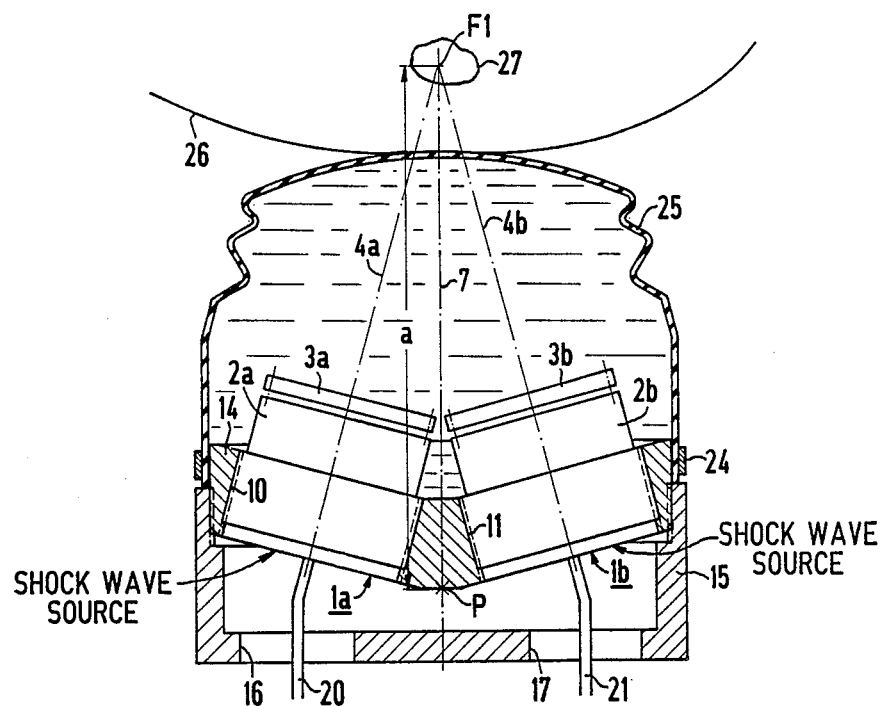
FIG. 1 is a side sectional view, taken along line I—I of FIG. 3, of an extracorporeal lithotripsy apparatus constructed in accordance with the principles of the present invention.
Figure 3:
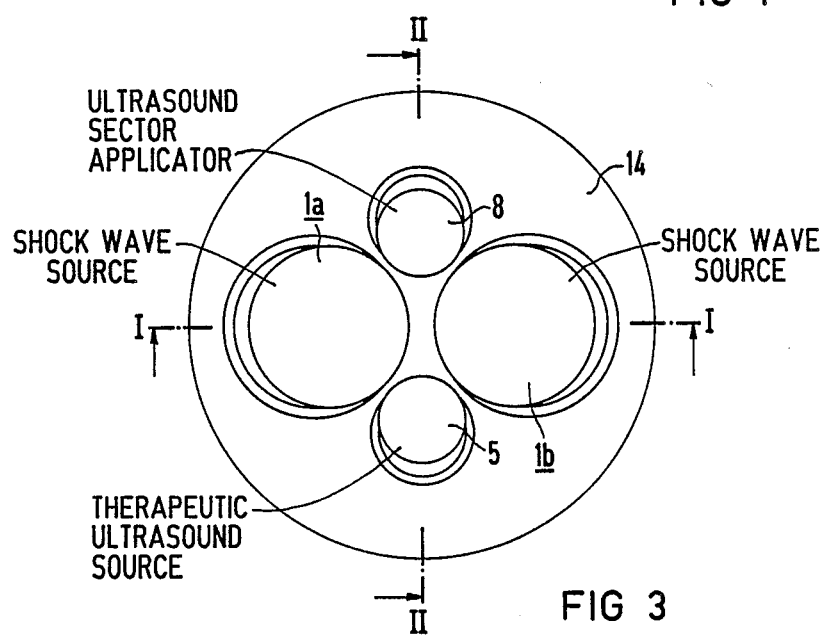
FIG. 3 is a schematic plane view of an extracorporeal lithotripsy apparatus constructed in accordance with the principles of the present invention, in a first embodiment.
Figure 2:
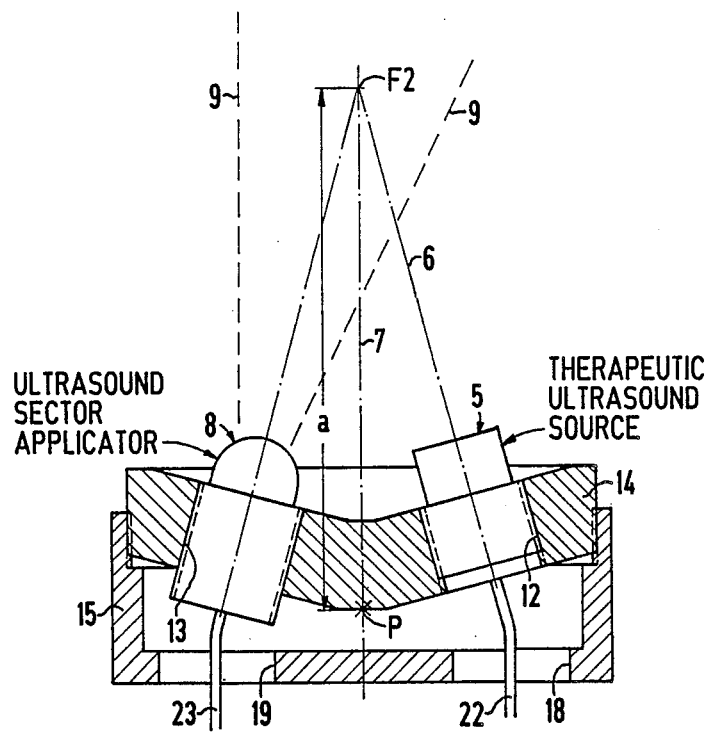
FIG. 2 is a side sectional view, with the coupling sack removed, taken along line II—II of FIG. 3 of an extracorporeal lithotripsy apparatus constructed in accordance with the principles of the present invention.

The structural components of a first embodiment of an extracorporeal lithotripsy apparatus constructed in accordance with the principals of the present invention are shown in FIGS. 1, 2 and 3. The apparatus includes one or more shock wave sources. In this embodiment, by way of example, two shock wave sources are schematically illustrated and generally referenced at $1a$ and $1b$. These shock wave sources may be constructed, for example, in accordance with the teachings of U.S. Pat. No. 4,674,505. The shock wave sources $1a$ and $1b$ each respectively include a shock wave tube $2a$ and $2b$ in which an acoustic focussing lens $3a$ and $3b$ is disposed. The shock wave sources $1a$ and $1b$ thus generate focused shock waves which converge in a focus zone lying on the respective acoustic axes $4a$ and $4b$ of the shock wave sources $1a$ and $1b$. The shock wave sources $1a$ and $1b$ are inclined relative to each other so that their acoustic axes $4a$ and $4b$ intersect, and such that the respective focus zones coincide. In FIG. 1, the center of the focus zones of the shock wave sources $1a$ and $1b$, corresponding to the intersection of the acoustic axes $4a$ and $4b$, is references F1.

The apparatus also includes a therapeutic ultrasound source which is positioned to generate focused ultrasound waves converging in a focus zone lying on the acoustic axis 6 of the therapeutic ultrasound source 5, as shown in FIG. 2. The therapeutic ultrasound source 5 is arranged relative to the shock wave sources $1a$ and $1b$ so that its acoustic axis 6 proceeds through the intersection of the acoustic axes $4a$ and $4b$ of the shock wave sources $1a$ and $1b$, and such that its focus zone coincides with the focus zones of the shock wave sources $1a$ and $1b$. This is illustrated in FIGS. 1 and 2 by showing the center F1 of the focus zones of the shock wave sources $1a$ and $1b$ (FIG. 1), and the center F2 of the focus zone of the therapeutic ultrasound source 5 (FIG. 2) as being the same distance "a" from a reference point P lying on the center axis 7 of the apparatus.

The apparatus may also include an ultrasound sector applicator 8 (schematically illustrated) which is part of an ultrasound locating system. The sector 9 is shown in FIG. 2, in the plane of the drawing, which can be swept using the ultrasound sector applicator 8. The ultrasound sector applicator 8 is arranged so that it sweeps a plane containing the acoustic axis 6 of the therapeutic ultrasound source, and thus sweeps the region surrounding the intersection of the acoustic axes 4a, 4b and 6 of the shock waves sources 1a and 1b and the therapeutic ultrasound source 5. Impediments, for example ribs, for the ultrasound waves emanating from the therapeutic ultrasound source 5 can thus be recognized.

The shock wave sources 1a and 1b and the therapeutic ultrasound source 5 together with the ultrasound sector applicator 8 (if present) are held in bores 10, 11, 12 and 13 of a common carrier 14 so that the above-described spatial arrangement is achieved. The shock wave sources 1a and 1b as well as the therapeutic ultrasound source 5 and the ultrasound sector applicator 8 (if present) lie diametrically opposite one another. The carrier 14 is received in a cylindrical housing 15 having a rear wall with openings 16, 17, 18 and 19 for the lines 20, 21, 22 and 23 respectively leading to the shock wave sources 1a and 1b, to the therapeutic ultrasound source 5 and to the ultrasound sector applicator 8. A flexible bellows 25 is attached with a clamp ring 24 to the circular circumference of the carrier 14, which projects slightly beyond the housing 15. The flexible bellows 25, as shown in FIG. 1, permits the apparatus to be pressed against the body 26 (schematically illustrated) of a patient such that a calculus 27 to be disintegrated is situated at the intersection of the acoustic axes 4a, 4b and 6. These positions of the apparatus and of the body 26 relative to each other are identified with the ultrasound sector applicator 8. To enable acoustic coupling of the apparatus to the body 26, thereby to introduce the shock waves from the shock wave sources 1a and 1b, the therapeutic ultrasound waves from the therapeutic ultrasound source 5, and the ultrasound locating pulses from the ultrasound sector applicator 8 into the body 26 of the patient with minimum energy loss, the space limited by the bellows 25 and the carrier 14 is filled with water or some other liquid coupling agent having an acoustic impedance matched to the acoustic impedance of the body 26 of the patient.

For clarity the ultrasound sector applicator is not shown in FIG. 1, afid the bellows 25 and the clamp ring 24 and the shock wave source 1a have not been shown in FIG. 2, and the housing 15 and the bellows 25 with the clamp ring 24 have not been shown in FIG. 3.

Figure 4:
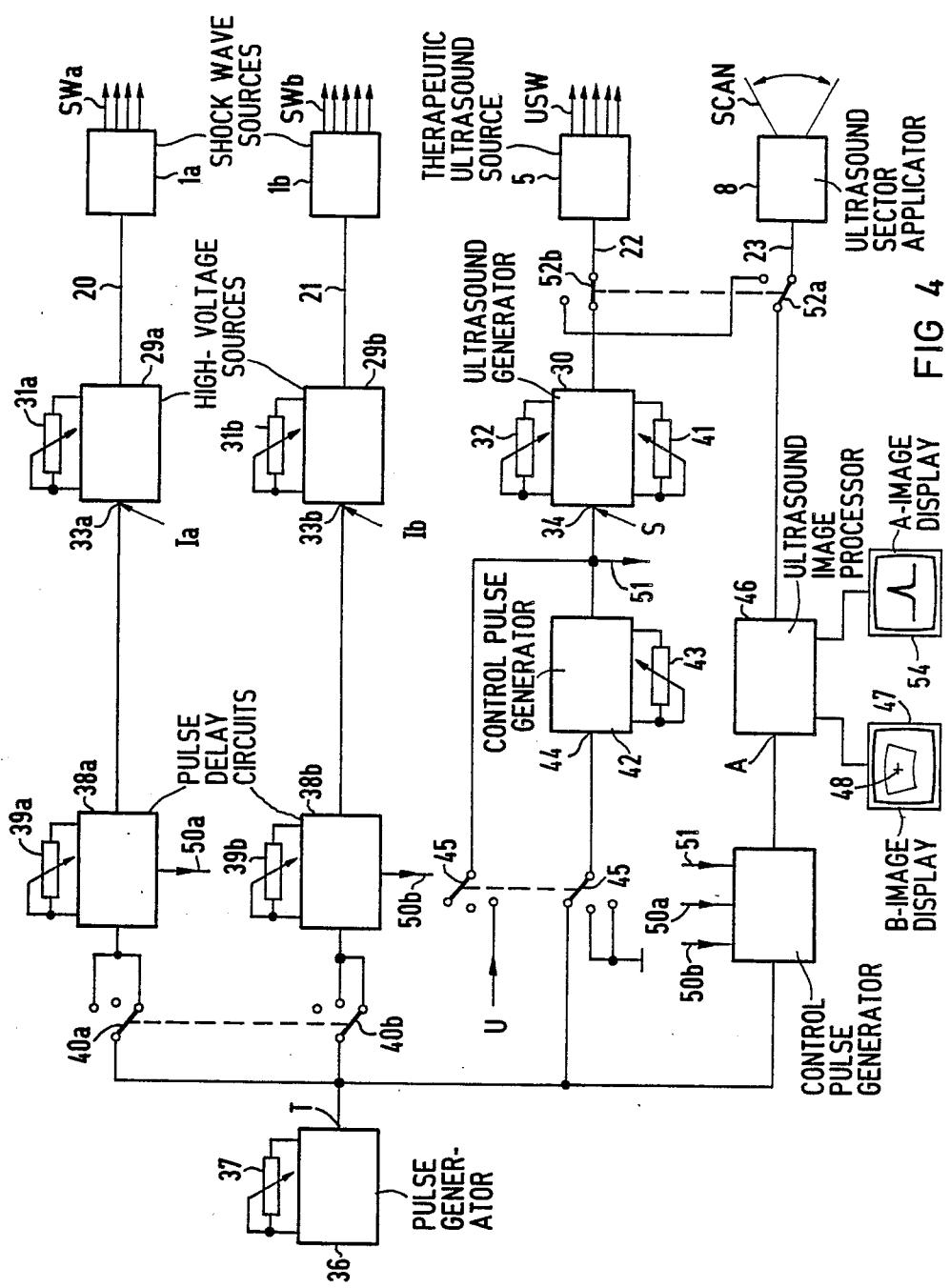
FIG. 4 is a schematic block diagram showing the generating stage used to drive the extracorporeal lithotripsy apparatus shown in FIGS. 1–3.

The calculus 27 to be disintegrated can thus be acted upon both with shock waves from the shock wave sources 1a and 1b and ultrasound waves emanating from the ultrasound source 5. The calculus 27 is located using the ultrasound sector application 8. All of these wave generators are driven by a generator stage as shown in FIG. 4, in which the shock wave sources 1a and 1b, the therapeutic ultrasound source 5 and the ultrasound sector applicator 8 are schematically indicated as blocks.

The generator stage includes high voltage sources 29a and 29b for respectively driving the shock wave sources 1a and 1b, and an ultrasound generator 30 for driving the therapeutic ultrasound source 5. The ultrasound generator 30, for example, may contain a radio-frequency generator as described in U.S. Pat. No. 4,315,514.

The high voltage sources 29a and 29b may be constructed as described in the aforementioned U.S. Pat. No. 4,674,505. In accordance therewith, the high voltage sources 29a and 29b each contain a high-voltage capacitor and a high-voltage supply which charges the capacitor. The output power of each of the high voltage sources 29a and 29b is variable so that the intensity of the shock waves SWa and SWb, respectively generated by the shock wave sources 1a and 1b, can be independently adjusted. Such adjustability is indicated by the variable resistors (potentiometers) 31a and 31b. Similarly, the output power of the ultrasound generator 30 can be varied by an adjustable resistor 32, so that the intensity of the therapeutic ultrasound wave USW from the therapeutic ultrasound source can be adjusted.

The high voltage sources 29a and 29b have respective trigger inputs 33a and 33b, by which they can be activated by respective trigger pulses Ia and Ib, where upon the respective shock wave sources 1a and 1b are driven. If the high voltage sources 29a and 29b each contain a high voltage capacitor, the trigger pulses 1a and 1b may, for example, actuate a high-voltage switch for connecting the respective charged capacitor to the respective shock wave source, which is then energized by a high voltage pulse.

The ultrasound generator 30 has a control input 34 by which it can be activated with a control pulse S so that the therapeutic is ultrasound source 5 is driven for a duration corresponding to the pulse length b (see FIG. 5) of the control pulse S. This may be achieved, for example, by suitable logic circuitry so that the ultrasound generator 30 is enabled only given the presence of a control pulse S.

Figure 5:
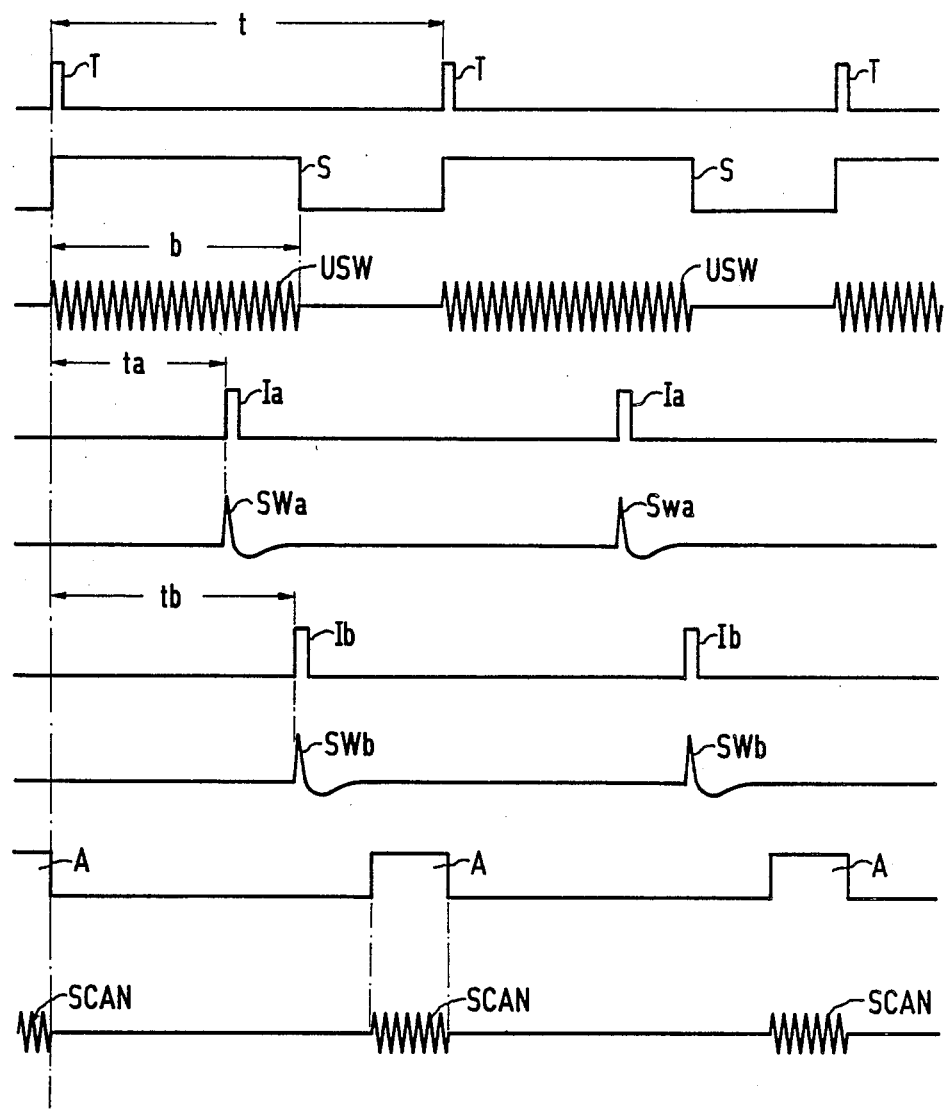
FIG. 5 is a graph showing signals at various locations in the generating stage of FIG. 4 for explaining the operation of the apparatus.

The generator stage 28 also includes further control circuitry, interacting with the high voltage sources 29a and 29b and the ultrasound generator 30, for the purpose of generating the trigger pulses Ia and Ib and the control pulse S and for selectively supplying those pulses to the appropriate devices. For this purpose, a pulse generator 36 is provided which generates periodic pulses T, as shown in FIG. 5, at intervals of t, with the interval t being variable, as indicated by an adjustment resistor 37 shown connected to the pulse generator 36.

Respective pulse delay circuits 38a and 38b are connected between the pulse generator 36 and the trigger inputs 33a and 33b of the high voltage sources 29a and 29b. Each pulse delay circuit 38a and 38b permits the pulse T generated by the pulse generator 36 to be delayed by a selected pulse delay time ta and tb, as shown in FIG. 5, before the trigger pulse 1a or 1b is released to the associated trigger input 33a or 33b. The pulse delay times ta and tb are variable, as schematically indicated by respective adjustment resistors 39a and 39b connected to the pulse delay circuits 38a and 38b.

Switches 40a and 40b, gang-coupled to each other, are connected between the pulse generator 36 and the inputs of the pulse delay circuits 38a and 38b. The switches 40a and 40b permit a pulse T to be supplied to the respective inputs of the pulse delay circuits 38a and 38b when the switches 40a and 40b are in the lower-most position, as shown in FIG. 4. This results in respective trigger pulses 1a and 1b being supplied, after the respective delays imposed by the pulse delay circuits 38a and 38b, to the high voltage sources 29a and 29b. If the switches 40a and 40b are in the middle switch position, only the high voltage source 29b receives a trigger pulse Ib. If the switches 40a and 40b are in their upper-most switch positions, only the high voltage source 29a receives a trigger pulse Ia. It is thus possible to selectively supply trigger pulses Ia or Ib to either one or both of the high voltage sources 29a and 29b, with a variable pulse delay time ta or tb being selected as desired.

A control pulse generator 42 is also provided for generating the control pulse S for the ultrasound generator 30. The pulse length b of the control pulse S is variable, as schematically indicated by an adjustment resistor 43 connected to the control pulse generator 42. The control pulse generator 42 has an input 44 connected to the pulse generator 36. The control pulse generator 42 is activateable via the input 44 so that it generates the control pulse S as an output given the presence of a pulse T.

Because the trigger pulses Ia and Ib for the high voltage sources 29a and 29b, as well as the control pulse S for the ultrasound generator 30, are derived from the same pulse T generated by the pulse generator 36, there is a defined chronological relationship between the output of the shock waves SWa and SWb and the output of the ultrasound waves USW. This chronological relationship can be varied as needed by suitable adjustment of the resistors 37, 39a, 39b and 43.

A dual output switch 45 is connected between the pulse generator 36 and the control pulse generator 42. The switch 45 permits the input 44 of the control pulse generator 42 to be disconnected from the pulse generator 36 and connected to ground when the switch 45 is in its middle switch position. The generation of ultrasound waves USW by the therapeutic ultrasound source 5 is then suppressed. When the switch 45 is moved to its lowest position, the input 44 of the control pulse generator 42 is still connected to ground, however, the control input 34 of the ultrasound generator 30 is connected to a potential U so that the control input 34 receives a continuous control signal. The ultrasound generator 30 thus drives the therapeutic ultrasound source 5 to generator continuous ultrasound waves USW as long as the switch 45 is in the lowest switch position.

The generator stage further includes an electronic ultrasound image processor 46 which is connected to the ultrasound sector applicator 8 for transmitting and receiving ultrasound locating pulses and echoes in a known manner. The ultrasound echoes received via the ultrasound applicator 8 and supplied to the ultrasound image processor 46 are used to construct a B-image of the scanned sector 9 which is visually portrayed on a display 47. A graticule 48, corresponding to the intersection of the acoustic axes 4a, 4b and 6, may be mixed into the ultrasound image of the scanned sector 9 on the display 47, so that a correct positioning of the apparatus relative to the body 26 of the patient is possible, by means of which the apparatus will be brought to a position so that the image of the calculus to be disintegrated coincides with the graticule 48.

The ultrasound image processor 46 is connected to a further control pulse generator 49 which generates activation pulses A, as shown in FIG. 5, which activate the ultrasound image processor 46, and thus the ultrasound sector applicator 8, to generate ultrasound images. The control circuit 49 is connected to the pulse generator 36 and generates an activation pulse A beginning at a point in time between two successive pulses T during which neither of the high voltage sources 29a or 29b is driving one of the shock wave sources 1a or 1b, and during which the ultrasound generator 30 is not driving the therapeutic ultrasound source 5. The control pulse S is therefore supplied to the control circuit 46 via line 51. The control circuit 46 is also connected to the delay circuits 38a and 38b via respective lines 50a and 50b and thereby receiving a signal identifying the duration of the pulse delay times ta and tb. The control circuit 49, after the occurrence of the leading edge of a pulse T, generates an activation pulse A in the absence of a signal from either of the pulse delay circuits 38a or 38b via the lines 50a and 50b and in the absence of a control pulse S via the line 51.

The ultrasound sector applicator 8 can be separated from the ultrasound image processor 46 by ganged switches 52a and 52b by bringing the switch 52a to its upper position, proceeding from the switch position shown in FIG. 4. This simultaneously causes the switch 52b between the ultrasound generator 30 and the therapeutic ultrasound source 5 to disconnect those units, and simultaneously connect the therapeutic ultrasound source 5 to the ultrasound image processor 46. The ultrasound image processor 46 can then, via the therapeutic ultrasound source 5, generate ultrasound A-images, which can be visually portrayed on a further display 54 connected to the ultrasound image processor 46. This permits further information to be obtained in addition to the information acquired via the ultrasound sector applicator 8.

The chronological relationship of all of the above-discussed signals is shown in FIG. 5. In the top line of FIG. 5, pulses T generated by the pulse generator 36 are shown, having a period t, which is variable, for example, between one second and a tenth of a second. Control pulses S having a pulse length b variable, for example, between ten microseconds and the period t of the pulses T are derived from the pulses T by the control pulse generator 42. The control pulses S activate the ultrasound generator 30 to drive the therapeutic ultrasound source 5 to generate ultrasound bursts USW, having a duration corresponding to the pulse length b of the control pulses S. The frequency of the ultrasound bursts is variable, for example, between 300 kHz and 2 MHz by a further adjustable resistor 41 connected to the ultrasound generator 30. The power density of the ultrasound bursts can be set between one and ten watts/cm$^2$.

The trigger pulses Ia and Ib for the high voltage sources 29a and 29b are derived from the pulses T by the voltage delay circuits 38a and 38b. The trigger pulses Ia and Ib are respectively delayed by delays ta and tb being variable between zero and the period t of the pulses T. The high voltage sources 29a and 29b respectively drive the shock wave sources Ia and Ib to deliver a shock wave SWa or SWb upon the occurrence of each trigger pulse Ia or Ib. The peak pressure of the shock wave SWA and Swb can be set between 20 and 150 Mpa. In the example shown in FIG. 5, the output of the shock waves SWa ensues during the second half of the duration of an ultrasound burst USW, whereas a shock wave SWb is generated immediately at the end of an ultrasound burst USW. Such an operating mode of the apparatus achieves a high effectiveness in calculus disintegration.

The activation pulses A derived by the control circuit 49 from the trigger pulse Ia and Ib and from the control pulses S activate the ultrasound sector applicator 8 to generate ultrasound images, with the ultrasound sector applicator 8 transmitting and receiving locating pulses. This is indicated in FIGS. 4 and 5 by the reference SCAN. As mentioned above and as shown in FIG. 5, production of an ultrasound image occurs when none of the shock wave sources 1a or 1b nor the therapeutic ultrasound source 5 are active, so that degrading of the ultrasound images due to the presence of shock waves of therapeutic ultrasound waves does not occur.

As is clear from the description relating to FIG. 4, operating modes for the apparatus deviating from the example shown in FIG. 5 are possible. For example, the pulse delay times ta and tb may be selected so that the output of shock waves SWa and SWb ensue simultaneously. Alternatively, the shock waves SWa and SWb can be made to occur at arbitrary points in time within a period t of the pulses T, in which the delay times ta and tb are correspondingly selected. There is also the possibility of generating only shock waves SWa or only shock waves SWb by appropriate actuation of the switches 40a and 40b. Further, treatment can be undertaken exclusively with shock waves SWa and/oder SWb by corresponding actuation of the shock 45. Additionally, by actuating the switch 45, it is possible to generate therapeutic ultrasound waves USW in a continuous form, with the therapeutic ultrasound waves being present for the entire duration of the treatment, or over individual sections of the treatment, with a periodic sequence of shock waves SWa and/or SWb being superimposed on the continuous therapeutic ultrasound waves. The mode of treatment which is selected can thus be optimally adapted to the nature of the calculus to be disintegrated. The operating mode of the ultrasound locating system can also be adapted to individual requirements, so that a B-image or an A-image can be obtained, either exclusively or in alternation.

Figure 6:
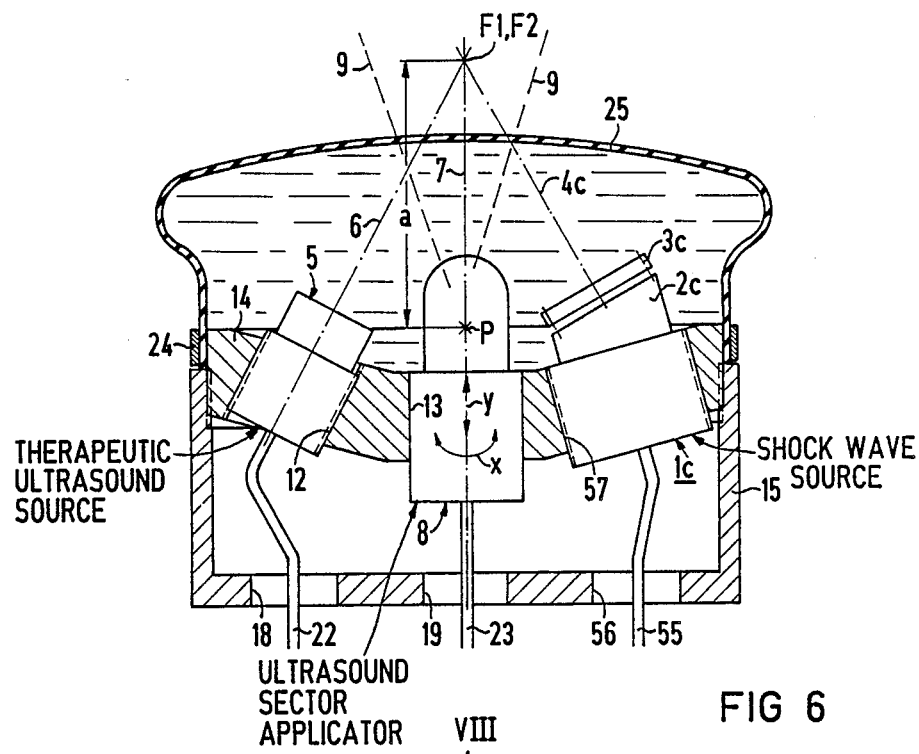
FIG. 6 is a side sectional view taken along line VI—VI of FIG. 7 of an extracorporeal lithotripsy apparatus constructed in accordance with the principles of the present invention.
Figure 7:
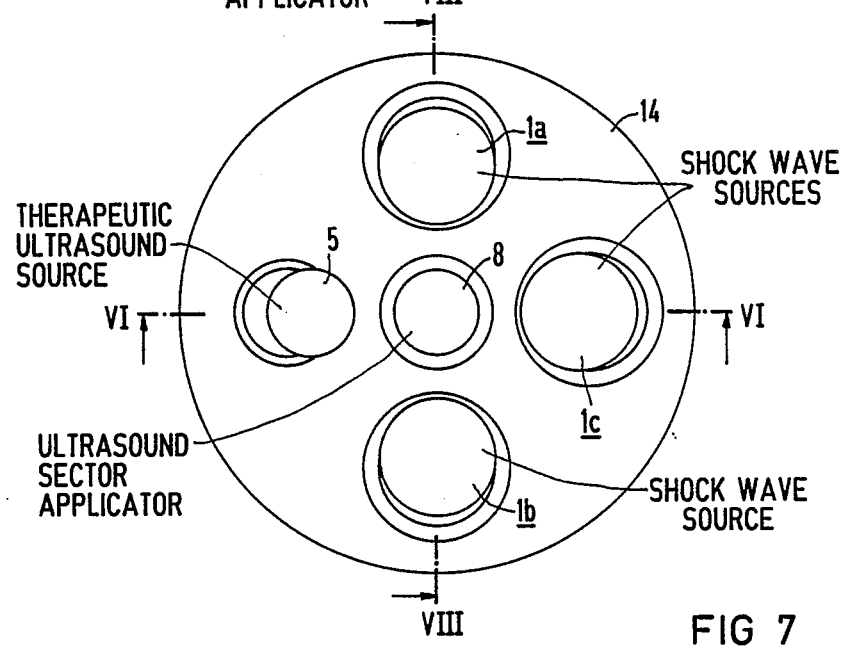
FIG. 7 is a schematic plan view of a second embodiment of a extracorporeal lithotripsy apparatus constructed in accordance with the principles of the present invention.
Figure 8:
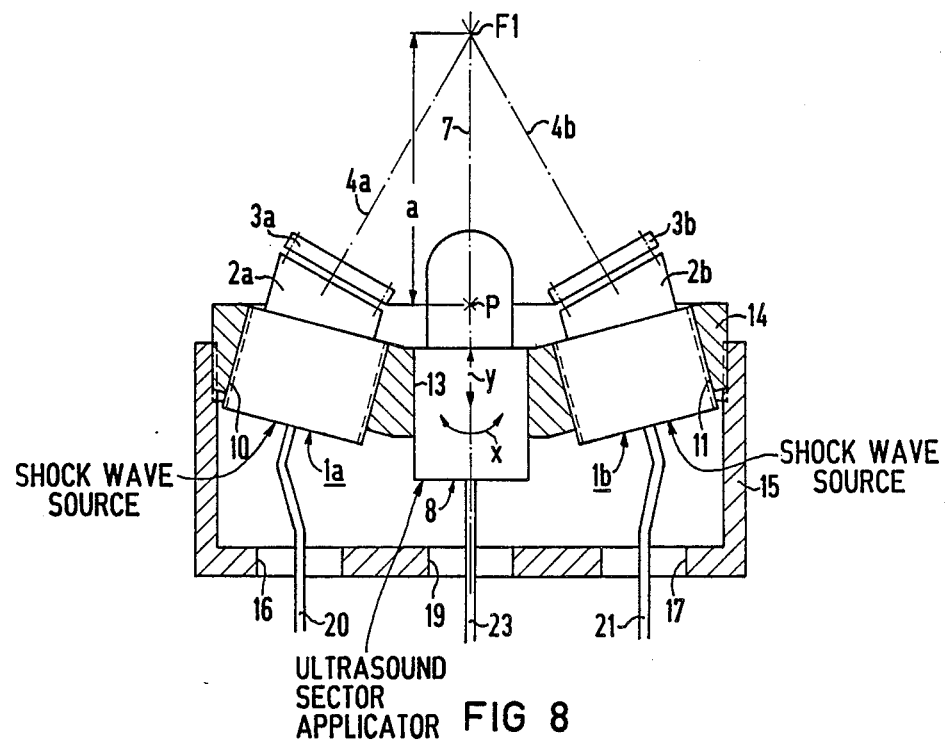
FIG. 8 is a side section view, with the coupling sack removed, taken along line VIII—VIII of FIG. 7 of an extracorporeal lithotripsy apparatus constructed in accordance with the principles of the present invention.

A further embodiment of the invention is shown in FIGS. 6-9, wherein parts and components identical to those described above are identified with the same reference symbols. In contrast to the embodiment of FIGS. 1-4, the embodiment shown in FIGS. 6-9 includes a third shock wave source 1c in addition to the shock wave source 1a and 1b. The third shock wave source 1c is disposed in a position to generate focused shock waves which converge in a focus zone lying on the acoustic axis 4c of the shock wave source 1c. A line 55 through an additional opening in the rear wall of the housing 15 leads to the shock wave source 1c. A therapeutic ultrasound source 5 is again provided, and is disposed in a position to emit focused ultrasound waves again converging in a focus zone on the acoustic axis 6 of the therapeutic ultrasound source 5. The shock wave sources 1a, 1b and 1c and therapeutic ultrasound source 5 are again received in respective bores of a common carrier 14, so that the shock wave sources 1a and 1b are diametrically opposite one another, whereas the therapeutic ultrasound source 5 is diametrically opposite the shock wave source 1c. The acoustic axes 4a, 4b and 4c are inclined relative to each other so as to intersect at a point on the center axis 7 of the apparatus. This intersection point corresponds to the centers of the focus zones of the shock wave sources 1a, 1b and 1c, referenced F1 in FIGS. 6 and 7. The therapeutic ultrasound source 5 is disposed so that its acoustic axis 6 proceeds through the intersection of the acoustic axes 4a, 4b and 4c, with the center F2 of its focus zone coinciding with the centers of the focus zones of the shock wave sources 1a, 1b and 1c. This is illustrated in FIGS. 6 and 7 by showing the centers F1 and F2 of the respective focus zones being disposed at the same distance "a" from a reference point P lying on the center axis 7 of the apparatus.

An ultrasound sector applicator 8 of an ultrasound locating means may again be provided in this embodiment, received in a central bore of the carrier 14, so that the sector 9 scanned by the applicator 8 contains the center axis 7 of the apparatus. The ultrasound sector applicator 8 is rotatably received in the carrier 14, as indicated by the curved double arrow x. It is thus possible to bring the ultrasound sector applicator 8 to a position in which the sector 9, shown in FIG. 6, contains the acoustic axes 4c and 6 of the shock wave source 1c and the therapeutic ultrasound source 5. The ultrasound sector applicator 8 may also be brought to a position wherein the sector 9 contains the acoustic axes 4a and 4b of the shock wave sources 1a and 1b. Impediments both for the ultrasound waves emanating from the therapeutic ultrasound source 5 and for the shock waves respectively emanating from the shock wave sources 1a, 1b and 1c can thus be recognized. The sector applicator 8 may also be displaced along the center axis 7 of the apparatus, as indicated by the double arrow y.

A flexible bellows 25 is again provided by means of which the apparatus can be pressed against the body (not shown) of a patient. The flexible bellows 25 is again attached with a clamp ring 24 to a circumference of the carrier 14. The volume limited by the bellows 25 and the carrier 14 is again filled with water or a suitable coupling medium.

The generator stage for the second embodiment is shown in FIG. 9, with the shock wave sources 1a, 1b and 1c (which generates shock waves SWc), the therapeutic ultrasound source 5 and the ultrasound sector applicator 8 being schematically shown as blocks. The operation of the generator stage in FIG. 9 is similar to that discussed in connection with FIG. 4, however, in the embodiment of FIG. 9 only a single high voltage source 29 is provided, which drives each of the shock wave sources 1a, 1b and 1c, which can be selectively connected individually or in groups by switches 53a, 53b and 53c. When two or more of the switches are closed, the connected shock wave sources simultaneously emit shock waves, when triggered. The output power of the high voltage source 29 can be adjusted by an adjustable resistor 31. The high voltage source 29 is supplied with a trigger pulse I causing one or more shock wave sources connected to the high voltage source 29 via a closed switch to be driven.

A single pulse delay circuit 38 is provided, which generates a pulse having a delay time variable by an adjustment resistor 39. In addition to the line 51 via which the control pulse S is supplied to the control circuit 49, only a single line 50 for the trigger pulse I is connected to the control circuit 49. The operation of the circuits shown in FIG. 9 is otherwise as described in connection with FIG. 4.

Although modifications and changes may be suggested by those skilled in the art, it is the intention of the inventors to embodiment within the patent warranted hereon all changes and modifications as reasonably and properly come within the scope of their contribution to the art.

We claim as our invention:

1. An extracorporeal lithotripsy apparatus comprising:
   means for generating shock waves focused in a first focus zone lying on an acoustic axis of said means for generating shock waves;
   means for generating therapeutic ultrasound waves converging in a second focus zone lying on an acoustic axis of said means for generating therapeutic ultrasound waves;

means for mounting said means for generating focused shock waves and said means for generating therapeutic ultrasound waves;

said means for generating focused shock waves and said means for generating therapeutic ultrasound waves being disposed in said means for mounting so that their respective acoustic axes intersect and said first and second focus zones substantially coincide;

means for coupling said focused shock waves and said therapeutic ultrasound waves into a body of a patient in which a calculus to be disintegrated is disposed; and means for driving said means for generating focused shock waves and said means for generating therapeutic ultrasound waves in a selected chronological sequence.

2. An apparatus as claimed in claim 1, wherein said means for driving includes means for selectively driving said means for generating focused shock waves and said means for generating therapeutic ultrasound waves simultaneously or in alternation.

3. An apparatus as claimed in claim 1, wherein said means for mounting comprises a common carrier in which both said means for generating focused shock waves and said means for generating therapeutic ultrasound waves are mounted.

4. An apparatus as claimed in claim 1, further comprising an ultrasound locating system for identifying the location of said calculus to be disintegrated, said ultrasound locating system including an ultrasound applicator held by said means for mounting and positioned to obtain an ultrasound image of a region surrounding said intersection of said acoustic axes of said means generating focused shock waves and said means for generating therapeutic ultrasound waves.

5. An apparatus as claimed in claim 4, wherein said ultrasound applicator is an ultrasound sector applicator being positioned for scanning a plane containing said acoustic axis of said means for generating focused shock waves.

6. An apparatus as claimed in claim 4, wherein said ultrasound applicator is an ultrasound sector applicator being positioned for scanning a plane containing said acoustic axis of said means for generating therapeutic ultrasound waves.

7. An apparatus as claimed in claim 4, wherein said ultrasound applicator is an ultrasound sector applicator being positioned for scanning a plane containing both acoustic axes of said means for generating focused shock waves and said means for generating therapeutic ultrasound waves.

8. An apparatus as claimed in claim 4, further comprising means for selectively connecting either said means for generating therapeutic ultrasound waves or said ultrasound applicator to said ultrasound locating system for transmitting and receiving ultrasound locating pulses and echoes for use in generating an ultrasound image of said calculus to be disintegrated.

9. An apparatus as claimed in claim 4, wherein said means for mounting comprises a common carrier in which said means for generating focused shock waves, said means for generating therapeutic ultrasound waves and said ultrasound applicator are mounted.

10. An apparatus as claimed in claim 1, wherein said means for driving comprises:

a generator means connected to said means for generating focused shock waves, said generator means having a trigger input and supplying an electric driving signal to said means for generating focused shock waves to cause a shock wave to be generated upon the occurrence of a trigger signal at said trigger input;

an ultrasound generator connected to said means for generating therapeutic ultrasound waves, said ultrasound generator having an ultrasound generator control input and supplying an electric ultrasound driving signal to said means for generating therapeutic ultrasound waves for the duration of an ultrasound generator control signal at said ultrasound generator control input;

a pulse generator which generates periodic pulses;

means for deriving said trigger signal from each periodic pulse of said pulse generator; and means for generating said ultrasound generator control signal.

11. An apparatus as claimed in claim 10, wherein said means for generating said control signal is a means for deriving a control pulse as said control signal from each periodic pulse of said pulse generator so that said means for generating therapeutic ultrasound waves is driven in bursts.

12. An apparatus as claimed in claim 11, wherein said means for driving further comprises:

means for disconnecting said means for deriving said control signal for said ultrasound generator from said pulse generator and for simultaneously supplying a continuous control signal to said ultrasound generator so that said means for generating therapeutic ultrasound waves is continuously driven.

13. An apparatus as claimed in claim 10, wherein said means for deriving said trigger signal includes means for introducing a selected delay in the generation of said trigger signal following each periodic pulse from said pulse generator.

14. An apparatus as claimed in claim 10, further comprising:

a housing containing said means for generating focused shock waves, said means for generating therapeutic ultrasound waves, said means for mounting and said means for coupling;

an ultrasound locating system including an ultrasound applicator disposed in said housing and an ultrasound image processor contained in said means for driving, said ultrasound applicator and receiving ultrasound locating pulses and echoes and supplying signals to said ultrasound image processor from which an ultrasound image of said focus zone is obtained, said ultrasound image processor having a processor control input and being enabled only upon the occurrence of a processor control signal at said control input; and a control pulse generator means having an output connected to said processor control input and respective inputs connected to said pulse generator, said means for deriving said trigger signal for said high voltage source and said means for deriving said ultrasound generator control signal for generating said processor control signal to enable said ultrasound image processor following each pulse from said pulse generator only in the absence of a trigger signal for said generator means and an ultrasound generator control signal.

15. An apparatus as claimed in claim 14, wherein said ultrasound applicator is an ultrasound sector applicator, and said apparatus further comprising:

means for disconnecting said ultrasound sector applicator from said ultrasound image processor and simultaneously connecting said means for generating therapeutic ultrasonic waves to said ultrasound image processor; and said ultrasound locating system including first and second visual displays and said ultrasound image processor generating an ultrasound B-image displayed on said first display means when connected to said ultrasound sector applicator and generating an ultrasound A-image displayed on said second display means when connected to said means for generating therapeutic ultrasound waves.

16. An extracorporeal lithotripsy apparatus comprising:

first means for generating focused shock waves converging in a first focus zone lying on an acoustic axis of said first means for generating focused shock waves;

second means for generating focused shook waves converging in a second focus zone lying on an acoustic axis of said second means for generating focused shock waves;

means for generating therapeutic ultrasound waves converging in a third focus zone lying on an acoustic axis of said means for generating therapeutic ultrasound waves, means for mounting said first and second means for generating focused shock waves and said means for generating therapeutic ultrasound waves;

said first and second means for generating focused shock waves and said means for generating therapeutic ultrasound waves being positioned in said means for mounting so that their respective acoustic axes intersect and so that said first, second and third focus zones substantially coincide, means for driving said first and second means for generating focused shock waves and said means for generating therapeutic ultrasound waves; and means for coupling said focused shock waves and said therapeutic ultrasound waves into a body of a patient in which a calculus to be disintegrated is disposed.

17. An apparatus as claimed in claim 16, further comprising an ultrasound locating system including an ultrasound applicator held by said means for mounting and positioned to obtain an ultrasound image of a region surround said intersection of said acoustic axes of said first and second means for generating focused shock waves and said means for generating therapeutic ultrasound waves.

18. An apparatus as claimed in claim 17, wherein said means for mounting comprises a common carrier in which said first and second means for generating focused shock waves, said means for generating therapeutic ultrasound waves and said ultrasound applicator are mounted.

19. An apparatus as claimed in claim 17, wherein said first and second means for generating focused shock waves are disposed in said means for mounting diametrically opposite each other and wherein said means for generating therapeutic ultrasound waves and said ultrasonic applicator are disposed in said means for mounting diametrically opposite each other.

20. An extracorporeal lithotripsy apparatus comprising:

first means for generating focused shock waves converging in a first focus zone lying on an acoustic axis of said first means for generating focused shock waves;

second means for generating focused shock waves converging in as second focus zone lying on an acoustic axis of said second means for generating focused shock waves;

third means for generating focused shock waves converging in a third focus zone lying on an acoustic axis of said third means for generating therapeutic ultrasound waves;

means for generating therapeutic ultrasound waves converging in a fourth focus zone lying on an acoustic axis of said means for generating therapeutic ultrasound waves;

means for mounting said first, second and third means for generating focused shock waves and said means for generating therapeutical ultrasound means said first, second, and third for generating focused shock waves and said means for generating therapeutic ultrasound waves being positioned in said means for mounting so that their respective acoustic axes intersect and such that said first, second, third and fourth focus zones substantially, coincide;

means for driving said first, second and third means for generating focused shock waves and said means for generating therapeutic ultrasound waves; and means for coupling said focused shock waves and said therapeutic ultrasound waves into a body of a patient in which a calculus to be disintegrated is disposed.

21. An apparatus as claimed in claim 20, further comprising an ultrasound locating system including an ultrasound applicator held by said means for mounting and positioned to transmit and receive ultrasound signals to obtain an ultrasound image of a region surrounding said intersection of said acoustic axes of said first, second and third means for generating focused shock waves and said means for generating therapeutic ultrasound waves.

22. An apparatus as claimed in claim 21, wherein said means for mounting comprises a common carrier in which said first, second and third means for generating focused shock waves, said means for generating therapeutic ultrasound waves and said ultrasound applicator are mounted.

23. An apparatus as claimed in claim 21, wherein said first and second means for generating focused shock waves are positioned diametrically opposite each other, wherein said third means for generating focused shock waves and said means for generating therapeutic ultrasound waves are disposed diametrically opposite each other, and wherein said ultrasound applicator is centrally disposed surrounded by said first, second and third means for generating focused shock waves and said means for generating therapeutic ultrasound waves.

* * * * *